United States Patent
Ramin

(10) Patent No.: US 6,333,025 B2
(45) Date of Patent: *Dec. 25, 2001

(54) USE OF NITROCELLULOSE AND CELLULOSE ESTER IN A NAIL VARNISH

(75) Inventor: Roland Ramin, Paris (FR)

(73) Assignee: L'Oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/434,120

(22) Filed: Nov. 5, 1999

(30) Foreign Application Priority Data

Nov. 6, 1998 (FR) .................................................. 98 14111

(51) Int. Cl.⁷ ..................................................... A61K 7/04

(52) U.S. Cl. ............................................. 424/61; 424/401

(58) Field of Search ................................................ 424/61

(56) References Cited

U.S. PATENT DOCUMENTS

| | | |
|---|---|---|
| 5,130,125 | 7/1992 | Martin et al. ........................... 424/61 |
| 5,424,061 | 6/1995 | Pappas et al. .......................... 424/61 |
| 5,578,297 | * 11/1996 | Mellul et al. ......................... 424/70.7 |
| 5,607,665 | 3/1997 | Callello et al. ........................ 424/61 |
| 5,639,447 | 6/1997 | Patel ...................................... 424/61 |
| 5,968,986 | * 10/1999 | Dyer ..................................... 514/643 |

FOREIGN PATENT DOCUMENTS

| | | |
|---|---|---|
| 0 432 572 | 6/1991 | (EP) . |
| WO 93/18098 | * 9/1993 | (WO) . |

\* cited by examiner

*Primary Examiner*—Thurman K. Page
*Assistant Examiner*—Liliana Di Nola-Baron
(74) *Attorney, Agent, or Firm*—Finnegan, Henderson, Farabow, Garrett & Dunner, L.L.P.

(57) ABSTRACT

Use of a cellulose ester for reducing the drying time of a nail varnish, wherein the nail varnish comprises, in a solvent medium, nitrocellulose a dyestuff, the cellulose ester being present in a synergistic amount, relative to the amount of nitrocellulose, effective for reducing the drying time of the nail varnish.

24 Claims, No Drawings

USE OF NITROCELLULOSE AND CELLULOSE ESTER IN A NAIL VARNISH

The present invention relates to the use of at least one cellulose ester for reducing the drying time of nail varnish compositions comprising nitrocellulose.

Nail varnish compositions generally comprise a film-forming polymer dissolved in an organic solvent medium. Film-forming polymers commonly used in these compositions include nitrocellulose. These compositions are generally applied as one or more coats to the surface of the nail, leading, after drying, to the formation of a film on the nail.

However, just after they have been applied, the coats of nail varnish can be damaged or degraded by contact, friction or touching foreign bodies such as, for example, clothing. Thus, it is desirable for these varnishes to dry quickly after they have been applied.

One method of improving the speed of drying of nail varnishes is the use of specific solvents. According to U.S. Pat. No. 5,424,061, acetone in combination with another co-solvent can be used to improve the speed of drying of nail varnish compositions. This combination, however, has as a constraint a limitation on the formulation of the nail varnish. Furthermore, solvents which are too volatile may be detrimental to the quality of the make-up effect obtained because defects may appear when applying the nail varnish. For example, lines may form on the coat of varnish, or the brush may dry excessively quickly during application. As a result, an inhomogeneous varnish coating is obtained that is not sufficiently smooth, lacks gloss, and has unsatisfactory staying power.

Another method of improving the speed of drying of nail varnishes is the use of specific additives. According to European Patent Application Number EP-A-432,572, silicone compounds can be used to improve the speed of drying of nail varnishes. European Patent Application Number EP-A-432,572 exemplifies combining other film-forming polymers with nitrocellulose to modify the cosmetic properties of the film of nail varnish.

Accordingly, an object of the present invention is to obtain a nitrocellulose-based nail varnish composition which has improved drying properties without using specific additives or solvents.

The inventor has discovered that the combination of nitrocellulose and at least one cellulose ester, in certain proportions, makes it possible to obtain a nail varnish with a drying time that is shorter than the drying time of similar compositions containing only nitrocellulose, or containing only cellulose ester as a film-forming polymer.

Contrary to the teaching of Example 4 of European Patent Application EP-A-432,572, which describes a nail varnish that has poor drying properties and which comprises nitrocellulose, an alkyd resin, and cellulose acetobutyrate, the inventor has discovered that the combination of nitrocellulose and cellulose acetobutyrate in a specific amount can have a synergistic effect on the drying time of the nail varnish composition.

Therefore, a subject of the invention is the use of a cellulose ester in a nail varnish composition comprising, in a solvent medium, a polymer system containing nitrocellulose; an additional film-forming polymer in an amount up to 50% by weight, relative to the total weight of nitrocellulose and cellulose ester; and a dyestuff in an amount which is sufficient to dye the composition, the cellulose ester being present in a synergistic amount relative to the amount of nitrocellulose effective for reducing the drying time of the composition.

The cellulose ester used according to the invention can comprise acyl groups chosen from R-CO- groups in which R is chosen from linear and branched alkyl radicals containing from 1 to 3 carbon atoms. For example, the cellulose ester can be chosen from cellulose acetates, cellulose acetopropionates, and cellulose acetobutyrates.

In an embodiment of the invention, the cellulose ester is chosen from cellulose acetobutyrates and cellulose acetopropionates.

Cellulose acetobutyrates can comprise a weight content of acetate groups ranging from 1 to 18% and a weight content of butyrate groups ranging from 30 to 60%. Cellulose acetobutyrates (referred to as CABs) which may be used in accordance with the invention are those sold under the names "CAB-551", "CAB-500", "CAB-553" and "CAB-381" by the company Eastern Chemical.

The weight contents of acetate and butyrate groups in these compounds are as follows:

| CAB product | Acetate content in % | Butyrate content in % |
|---|---|---|
| CAB-551 | 2 | 53 |
| CAB-500 | 5 | 49 |
| CAB-553 | 2 | 47 |
| CAB-381 | 13 | 37 |

Cellulose acetobutyrates can be present in the nail varnish composition of the invention in a weight content ranging from 10% to 80% by weight relative to the total weight of cellulose ester and nitrocellulose.

In an embodiment of the invention, when the weight content of acetate groups is less than or equal to 5%, the cellulose acetobutyrate is present in the nail varnish composition in an amount ranging from 10% to 30% by weight, relative to the total weight of cellulose ester and nitrocellulose. In another embodiment of the invention, when the weight content of acetate groups is less than or equal to 5%, the cellulose acetobutyrate is present in the nail varnish composition in an amount ranging from 12.5% to 25% by weight, relative to the total weight of cellulose ester and nitrocellulose.

In yet another embodiment of the invention, when the weight content of acetate groups is greater than or equal to 10%, the cellulose acetobutyrate is present in an amount ranging from 20% to 80% by weight, relative to the total weight of cellulose ester and nitrocellulose present in the composition. In a further embodiment of the invention, when the weight content of acetate groups is greater than or equal to 10%, the cellulose acetobutyrate is present in an amount ranging from 25% to 75% by weight, relative to the total weight of cellulose ester and nitrocellulose present in the composition.

Cellulose acetopropionates can comprise a weight content of acetate groups ranging from 1 to 5% and a weight content of propionate groups ranging from 35 to 50%. Cellulose acetopropionates (referred to as CAPs) the company Eastman Chemical. which may be used are those sold under the names "CAP-482-0.5", "CAP-482-20" and "CAP-504" by the company Eastman Chemical.

The weight content of acetate and propionate groups in these compounds are as follows:

| CAP product | Acetate content in % | Propionate content in % |
|---|---|---|
| CAP-482-0.5 | 2.5 | 44 |
| CAP-482-20 | 2.5 | 46 |
| CAP-504 | 2.5 | 40 |

The nitrocellulose used according to the invention can be chosen from nitrocellulose RS ⅛ sec.; RS ¼ sec.; RS ½ sec.; RS 5 sec.; RS 15 sec.; RS 35 sec.; RS 75 sec.; RS 150 sec.; AS ¼ sec.; AS ½ sec.; SS ¼ sec.; SS ½ sec.; and SS 5 sec., sold in particular by the company Hercules.

In an embodiment of the invention, cellulose acetopropionates can be present in the nail varnish composition in an amount ranging from 10% to 80% by weight, relative to the total weight of cellulose ester and nitrocellulose present in the composition. In another embodiment of the invention, cellulose acetopropionates can be present in the nail varnish composition in an amount ranging from 12.5% to 75% by weight, relative to the total weight of cellulose ester and nitrocellulose present in the composition.

Nitrocellulose can be present in the composition in an amount ranging from 1.5 to 35% by weight relative to the total weight of the composition. In another embodiment, the nitrocellulose can be present in the composition in an amount ranging from 8% to 20% by weight, relative to the total weight of the composition.

According to an embodiment of the invention, the only film-forming polymers present in the composition are nitrocellulose and cellulose ester, as defined above.

According to another embodiment of the invention, the composition comprises at least one film-forming polymer in addition to the nitrocellulose and cellulose ester, at least to improve the cosmetic and physicochemical properties of nail varnish film.

The at least one additional film-forming polymer can be chosen from polyvinyl butyrals, alkyd resins, resins resulting from the condensation of formaldehyde with an arylsulphonamide, polyesters, polyurethanes, polyester-polyurethanes, polyether-polyurethanes, and radical-generated polymers. Examples of radical-generated polymers include polymers of acrylic, acrylic-strene and/or vinyl type, and mixtures thereof.

In yet another embodiment of the invention, the additional film-forming polymer can be present in the nail varnish composition in an amount up to 50% by weight, and is preferably present in an amount less than 40% by weight, relative to the total weight of nitrocellulose and cellulose ester. In still another embodiment of the invention, the amount of additional film forming polymer ranges from 1% to 15% by weight relative to the total weight of nitrocellulose and cellulose ester.

The solvent medium for the nail varnish composition can comprise at least one organic solvent.

Examples of organic solvents which can be used in the invention include:

ketones which are liquid at room temperature, such as methyl ethyl ketone, methyl isobutyl ketone, diisobutyl ketone, isophorone, cyclohexanone and acetone;

alcohols which are liquid at room temperature, such as ethanol, isopropanol, diacetone alcohol, 2-butoxyethanol and cyclohexanol;

glycols which are liquid at room temperature, such as ethylene glycol, propylene glycol, pentylene glycol and glycerol;

propylene glycol ethers which are liquid at room temperature, such as propylene glycol monomethyl ether, propylene glycol monomethyl ether acetate and dipropylene glycol mono-n-butyl ether;

short-chain esters (containing from 3 to 8 carbon atoms in total), such as ethyl acetate, methyl acetate, propyl acetate, n-butyl acetate and isopentyl acetate;

ethers which are liquid at room temperature, such as diethyl ether, dimethyl ether and dichlorodiethyl ether;

alkanes which are liquid at room temperature, such as decane, heptane, dodecane and cyclohexane;

aromatic cyclic compounds which are liquid at room temperature, such as toluene and xylene;

aldehydes which are liquid at room temperature, such as benzaldehyde and acetaldehyde, and mixtures thereof.

Compositions according to the invention can further comprise water in an amount ranging up to 10% by weight, relative to the total weight of the composition.

Compositions according to the invention may also comprise at least one plasticizer. Examples of plasticizers suitable for use in the present invention, alone or as a mixture, include:

glycols and derivatives thereof such as diethylene glycol ethyl ether, diethylene glycol methyl ether, diethylene glycol butyl ether, diethylene glycol hexyl ether, ethylene glycol ethyl ether, ethylene glycol butyl ether and ethylene glycol hexyl ether;

glycerol esters;

propylene glycol derivatives including propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether and propylene glycol butyl ether;

acid esters, including carboxylic acid esters, such as citrates, phthalates, adipates, carbonates, tartrates, phosphates and sebacates;

oxyethylenated derivatives, including oxyethylenated oils, for example, plant oils such as castor oil; and mixtures thereof.

The amount of plasticizer can be chosen by a person skilled in the art on the basis of his or her general knowledge, so as to obtain a composition which has cosmetically acceptable properties. The amount of plasticizer present in the composition can range, for example, from 0.5% to 20% by weight relative to the total weight of the composition. In an embodiment of the invention, the amount of plasticizer ranges from 2% to 10% by weight relative to the total weight of the composition.

The dyestuff present in the composition can be chosen from pulverulent compounds and dyes which are soluble in the solvent medium of the composition, in an amount which is sufficient to dye the varnish in a Collor in the visible wavelength range, i.e. between 400 and 800 nm, and, for example, in a content ranging from 0.001% to 10% by weight relative to the total weight of the composition. The pulverulent compounds can be chosen from the pigments, nacres and glitter flakes usually used in nail varnishes.

The pigments can be white or colored, and inorganic or organic. Examples of inorganic pigments include titanium dioxide, which has optionally been surface-treated, zirconium oxide and cerium oxide, as well as iron oxide and chromium oxide, manganese violet, ultramarine blue, chromium hydrate and ferric blue, and metallic pigments such as aluminium and bronze. Examples of organic pigments include carbon black, pigments of D&C type and lakes based on cochineal carmine, barium, strontium, calcium, aluminium, and guanine.

The nacreous pigments can be chosen from white nacreous pigments such as mica coated with titanium or with bismuth oxychloride, colored nacreous pigments such as titanium mica with, for example, iron oxides, ferric blue, chromium oxide, or with an organic pigment of the above-mentioned type, as well as nacreous pigments based on bismuth oxychoride.

The glitter flakes can be chosen from those made of acrylic, of polyester and of polyethylene terephthalate, and of aluminium.

The dyes are, for example, Sudan red, DC Red 17, DC Green 6, α-carotene, soybean oil, Sudan brown, DC Yellow 11, DC Violet 2, DC Orange 5 and cannelloni yellow.

Compositions of the invention can also optionally comprise an optical brightener, for example to reduce the yellowing effect of the nitrocellulose and consequently of the composition, this brightener not being considered, for the purposes of the invention, as a dyestuff. One brightener which can be used is the monosodium salt of alizurol purple; this brightener can be present in the inventive compositions in an amount ranging from $10^7$% to $10^4$% by weight relative to the total weight of the composition.

Compositions according to the invention can also comprise any additive known to those skilled in the art capable of being incorporated into dye compositions. Such additives include thickeners, spreading agents, wetting agents, dispersing agents, antifoaming agents, preserving agents, UV screening agents, active agents, surfactants, moisturizers, fragrances, neutralizers, stabilizers, and antioxidants. Needless to say, a person skilled in the art will take care to select this or these optional additional compounds, and/or the amount thereof, such that the advantageous properties of the composition for the use according to the invention are not, or are not substantially, adversely affected by the addition envisaged. In an embodiment of the invention, the composition is free or essentially free of silicone drying agents.

Compositions according to the invention can be prepared by a person skilled in the art on the basis of his or her general knowledge and according to the prior art.

The invention is illustrated in greater detail by the non-limiting examples below.

The drying time of the compositions was evaluated under the following conditions:

A film of composition 300 μm thick was applied to a glass plate, heated to 30° C., and the apparent drying time of the film was determined using a Beck and Koller machine. Four measurements were taken and the average drying time, expressed in minutes, was calculated.

EXAMPLES 1 TO 24

The 24 non-colored compositions below were prepared:

| Nitrocellulose ½ sec. | x g |
| Cellulose ester | y g |
| Acetyl tributyl citrate | 4.5 g |
| N-ethyl o,p-toluenesulphonamide | 3.6 g |
| Ethyl acetate qs | 100 g | a) Cellulose ester: cellulose acetobutyrate 381-0.5 from Eastman Chemical

| Example | Nitrocellulose x | CAB 381-0.5 y | Drying time |
|---|---|---|---|
| 1 (NWI) | 20 | 0 | 3.1 |
| 2 (NWI) | 17.5 | 2.5 | 3.1 |
| 3 | 15 | 5 | 2.35 |
| 4 | 10 | 10 | 2.4 |
| 5 | 5 | 15 | 2.7 |
| 6 (NWI) | 0 | 20 | 3.5 |

NWI means not "within the invention"
CAB means cellulose acetobutyrate

It was found that the drying time of compositions 3 to 5 was less than that of composition 1, which contained only nitrocellulose as the film-forming polymer component and less than that of Example 6, which contained only cellulose acetobutyrate as film-forming polymer.

b) Cellulose ester: cellulose acetobutyrate 551-0.01 from Eastman Chemical

| Example | Nitrocellulose x | CAB 551-0.01 y | Drying time |
|---|---|---|---|
| 7 (NWI) | 20 | 0 | 3.1 |
| 8 | 17.5 | 2.5 | 2.5 |
| 9 | 15 | 5 | 2.7 |
| 10 (NWI) | 10 | 10 | 3.1 |
| 11 (NWI) | 5 | 15 | 3.2 |
| 12 (NWI) | 0 | 20 | 3.1 |

It was found that the drying time of compositions 8 and 9 was less than that of composition 7, which contained only nitrocellulose as the film-forming polymer component, and was less than that of Example 12, which contained only cellulose acetobutyrate as the film-forming polymer component.

c) Cellulose ester: cellulose acetobutyrate 318-20 from Eastman Chemical

| Example | Nitrocellulose x | CAB 381-20 y | Drying time |
|---|---|---|---|
| 13 (NWI) | 20 | 0 | 3.1 |
| 14 | 17.5 | 2.5 | 2.3 |
| 15 | 15 | 5 | 2.15 |
| 16 | 10 | 10 | 2.1 |
| 17 | 5 | 15 | 2.9 |
| 18 (NWI) | 0 | 20 | 3.2 |

It was found that the drying time of compositions 14 to 17 was less than that of composition 13, which contained only nitrocellulose as the film-forming polymer component, and was less than that of Example 18, which contained only cellulose acetobutyrate as the film-forming polymer component.

d) Cellulose ester: cellulose acetopropionate 482-0.5 from Eastman Chemical

| Example | Nitrocellulose x | CAP y | Drying time |
|---|---|---|---|
| 19 (NWI) | 20 | 0 | 3.1 |
| 20 | 17.5 | 2.5 | 2.35 |
| 21 | 15 | 5 | 2.05 |
| 22 | 10 | 10 | 2.15 |

-continued

| Example | Nitrocellulose x | CAP y | Drying time |
|---------|------------------|-------|-------------|
| 23      | 5                | 15    | 2.3         |
| 24 (NWI)| 0                | 20    | 2.45        |

CAP means cellulose acetopropionate

It was found that the drying time of compositions 20 to 23 was less than that of composition 19, which contained only nitrocellulose as the film-forming polymer component and was less than that of Example 24, which contained only cellulose acetopropionate as the film-forming polymer component.

EXAMPLE 25

A colored nail varnish having the composition below was prepared:

| | |
|---|---|
| Nitrocellulose ½ sec. | 15 g |
| Cellulose acetobutyrate 381-0.5 | 5 g |
| Acetyl tributyl citrate | 4.5 g |
| N-ethyl o,p-toluenesulphonamide | 3.6 g |
| Hectorite | 1.2 g |
| Isopropyl alcohol | 8 g |
| Pigments | 1.5 g |
| Solvents | 100 g |
| (ethyl acetate, butyl acetate) qs | |

The varnish applied easily to the nail and dried quickly.

What is claimed is:

1. A process for reducing the drying time of a nail varnish composition, said process comprising:
combining at least one cellulose ester with a nail varnish to form a nail varnish composition, said nail varnish composition comprising, in a solvent medium, said at least one cellulose ester, a film-forming polymer, and a dyestuff, wherein said film-forming polymer is nitrocellulose, wherein said dyestuff is present in said composition in an amount sufficient to dye said composition, and wherein said cellulose ester is combined with said nail varnish in a synergistically effective amount, relative to the amount of nitrocellulose, for reducing the drying time of said nail varnish composition.

2. A process according to claim 1, wherein said nail varnish composition further comprises at least one second film-forming polymer which is other than nitrocellulose and other than a cellulose ester and is present in said nail varnish composition in an amount up to 50% by weight relative to the total weight of said nitrocellulose and said cellulose ester.

3. A process according to claim 2, wherein said at least one second film-forming polymer is present in said composition in an amount ranging from greater than 0% up to 40% by weight relative to the total weight of said nitrocellulose and said cellulose ester.

4. A process according to claim 1, wherein said cellulose ester comprises acyl groups chosen from R-CO- groups wherein R is chosen from linear and branched alkyl radicals containing from 1 to 3 carbon atoms.

5. A process according to claim 1, wherein said cellulose ester is chosen from cellulose acetates, cellulose acetopropionates, and cellulose acetobutyrates.

6. A process according to claim 5, wherein said cellulose ester is a cellulose acetobutyrate.

7. A process according to claim 6, wherein said cellulose acetobutyrate is present in said composition in an amount ranging from 10% to 80% by weight relative to the total weight of cellulose ester and nitrocellulose present in said composition.

8. A process according to claim 6, wherein said cellulose acetobutyrate comprises a weight content of acetate groups ranging from 1 to 18% and a weight content of butyrate groups ranging from 30 to 60%.

9. A process according to claim 6, wherein said cellulose acetobutyrate comprises a weight content of acetate groups of less than or equal to 5% and is present in said composition in an amount ranging from 10% to 30% by weight relative to the total weight of cellulose ester and nitrocellulose.

10. A process according to claim 6, wherein said cellulose acetobutyrate comprises a weight content of acetate groups of greater than or equal to 10% and is present in said composition in an amount ranging from 20% to 80% by weight relative to the total weight of cellulose ester and nitrocellulose.

11. A process according to claim 5, wherein said cellulose ester is a cellulose acetopropionate.

12. A process according to claim 11, wherein said cellulose acetoproprionate is present in said composition in an amount ranging from 10% to 80% by weight relative to the total weight of cellulose ester and nitrocellulose present in said composition.

13. A process according to claim 11, wherein said cellulose acetopropionate comprises a weight content of acetate groups ranging from 1 to 5% and a weight content of propionate groups ranging from 35 to 50%.

14. A process according to claim 1, wherein said nitrocellulose is present in said composition in an amount ranging from 1.5 to 35% by weight relative to the total weight of the composition.

15. A process according to claim 14, wherein said nitrocellulose is present in said composition in an amount ranging from 8% to 20% by weight relative to the total weight of the composition.

16. A process according to claim 1, wherein said at least one second film-forming polymer is chosen from polyvinyl butyrals, alkyd resins, resins resulting from the condensation of formaldehyde with an arylsulphonamide, polyesters, polyurethanes, polyester-polyurethanes, polyether-polyurethanes, and radical-generated polymers.

17. A process according to claim 16, wherein said radical-generated polymers are chosen from acrylic, acrylic-styrene, and vinyl type polymers.

18. A process according to claim 1, wherein said at least one additional film-forming polymer is present in said composition in an amount ranging from 1% to 15% by weight relative to the total weight of nitrocellulose and cellulose ester present in said composition.

19. A process according to claim 1, wherein said dyestuff is chosen from dyes, pigments and glitter flakes, and wherein said dyestuff is soluble in the solvent medium for the composition.

20. A process according to claim 1, wherein said dyestuff is present in said composition in an amount ranging from 0.001% to 10% by weight relative to the total weight of the composition.

21. A process according to claim 1, wherein said solvent medium comprises at least one organic solvent.

22. A process according to claim 1, wherein said composition further comprises at least one plasticizer.

23. A process according to claim 1, wherein said composition is essentially free of silicone drying agent.

24. A process according to claim 23, wherein said composition is free of silicone drying agent.

* * * * *

UNITED STATES PATENT AND TRADEMARK OFFICE
CERTIFICATE OF CORRECTION

PATENT NO.    : 6,333,025 B2
DATED         : December 25, 2001
INVENTOR(S)   : Roland Ramin It is certified that error appears in the above-identified patent and that said Letters Patent is hereby corrected as shown below:

<u>Title page,</u>
Item [57], ABSTRACT,
Line 3, after "nitrocellulose" insert -- and --.

<u>Column 5,</u>
Line 10, "oxychoride" should be -- oxychloride --.
Line 67, insert -- with x + y = 20 g --.

Signed and Sealed this

First Day of July, 2003

JAMES E. ROGAN
*Director of the United States Patent and Trademark Office*